United States Patent
Kim

(10) Patent No.: US 9,813,597 B2
(45) Date of Patent: Nov. 7, 2017

(54) GAZE TRACKER AND METHOD FOR TRACKING GAZE THEREOF

(71) Applicant: HYUNDAI MOTOR COMPANY, Seoul (KR)

(72) Inventor: Seon A Kim, Seoul (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 114 days.

(21) Appl. No.: 14/945,114

(22) Filed: Nov. 18, 2015

(65) Prior Publication Data
US 2017/0083746 A1    Mar. 23, 2017

(30) Foreign Application Priority Data

Sep. 21, 2015 (KR) .................. 10-2015-0133308

(51) Int. Cl.
*G06K 9/00* (2006.01)
*H04N 5/225* (2006.01)
(Continued)

(52) U.S. Cl.
CPC ......... *H04N 5/2256* (2013.01); *A61B 3/0025* (2013.01); *A61B 3/113* (2013.01); *A61B 3/14* (2013.01); *A61B 3/154* (2013.01); *A61B 5/18* (2013.01); *G06K 9/00604* (2013.01); *H04N 5/2258* (2013.01); *H04N 13/0239* (2013.01); *G06K 9/00845* (2013.01)

(58) Field of Classification Search
CPC ........... G06K 9/00597; G06K 9/00604; G06K 9/0061; G06K 9/00845; G06K 2209/401; G06T 7/70; G06T 7/73; G06T 2207/30041; A61B 3/0008; A61B 3/0025; A61B 3/113; A61B 3/14; A61B 3/145
See application file for complete search history.

(56) References Cited

U.S. PATENT DOCUMENTS 5,835,797 A * 11/1998 Odaka .............................. 396/51
8,077,914 B1 * 12/2011 Kaplan ......................... 382/103
(Continued)

FOREIGN PATENT DOCUMENTS

JP    2005-185431 A    7/2005
JP    2010-204823 A    9/2010
(Continued)

*Primary Examiner* — Andrew W Johns
(74) *Attorney, Agent, or Firm* — Brinks Gilson & Lione

(57) ABSTRACT

The present disclosure provides a gaze tracker and a gaze tracking method. The gaze tracker includes: an image acquirer to acquire eye images of a user using two or more cameras and two or more lightings; and a gaze calculator which detects a lighting reflection point from each eye image to extract a cornea central point, detects a pupil central point from each eye image, and calculates a gaze vector. In particular, when lighting reflection points are detected from each eye image, the gaze calculator calculates vectors for connection between each lighting and a corresponding lighting reflection point and detects an intersection point between the calculated vectors. When only one lighting reflection point is detected, the gaze calculator extracts the cornea central point using distance information between a pre-stored lighting reflection point and the cornea central point and the one lighting reflection point.

14 Claims, 4 Drawing Sheets

(51) Int. Cl.
*A61B 3/113* (2006.01)
*A61B 3/14* (2006.01)
*A61B 3/00* (2006.01)
*A61B 5/18* (2006.01)
*H04N 13/02* (2006.01)
*A61B 3/15* (2006.01)

(56) References Cited

U.S. PATENT DOCUMENTS

| | | |
|---|---|---|
| 8,824,779 B1* | 9/2014 | Smyth ............................ 382/154 |
| 2013/0002846 A1* | 1/2013 | De Bruijn et al. .............. 348/78 |
| 2013/0050833 A1* | 2/2013 | Lewis et al. ................... 359/630 |
| 2014/0240675 A1* | 8/2014 | Narasimha-Iyer et al. .................... A61B 3/0025 351/210 |
| 2016/0063304 A1* | 3/2016 | Yamashita ............ G06K 9/0061 348/78 |
| 2016/0063326 A1* | 3/2016 | Yamashita et al. .................. G06K 9/00604 348/78 |
| 2016/0086338 A1* | 3/2016 | Nagamatsu et al. .. G06T 7/0044 348/78 |

FOREIGN PATENT DOCUMENTS

| | | |
|---|---|---|
| JP | 2010-259605 A | 11/2010 |
| KR | 10-0820639 B1 | 4/2008 |
| KR | 10-2012-0055011 A | 5/2012 |
| KR | 10-2014-0126419 A | 10/2014 |

* cited by examiner

GAZE TRACKER AND METHOD FOR TRACKING GAZE THEREOF

CROSS-REFERENCE TO RELATED APPLICATION

This application claims the benefit of Korean Patent Application No. 10-2015-0133308, filed on Sep. 21, 2015, which is incorporated herein by reference in its entirety.

FIELD

The present disclosure relates to a gaze tracker and a gaze tracking method for tracking user gaze.

BACKGROUND

The statements in this section merely provide background information related to the present disclosure and may not constitute prior art.

Gaze tracking has been applied in various fields such as driver state monitoring, intent recognition, and device control in a gaze interworking vehicle. Recently, gaze tracking has been applied to monitor attention dispersion of a driver.

Such a gaze tracker captures an eye image using a stereo camera and detects two lighting reflection points from the captured eye image. In addition, the gaze tracker calculates a central point of a cornea using the two detected lighting reflection points and calculates a gaze direction of a user using the calculated central point of the cornea and a central point of a pupil.

However, we have discovered that a conventional gaze tracker is capable of tracking gaze only when two lighting reflection points are generated in an iris, and thus when only one lighting reflection point is generated in an iris due to a face angle, it is not possible to track gaze to excessively and narrowly limit a gaze tracking range.

SUMMARY

The present disclosure provides a gaze tracker and a gaze tracking method, for tracking user gaze even if only one reflection point is formed at a cornea during gaze tracking using a stereo camera including two cameras and two lightings.

A gaze tracker includes an image acquirer configured to acquire eye images of a user using two or more cameras and two or more lightings, and a gaze calculator configured to detect a lighting reflection point from each eye image to extract a cornea central point, to detect a pupil central point from each eye image, and to calculate a gaze vector using the cornea central point and the pupil central point, in which, when two or more lighting reflection points are detected from each of the eye images, the gaze calculator calculates vectors for connection between each lighting and a lighting reflection point corresponding thereto and detects an intersection point between the calculated vectors as the cornea central point, and when only one lighting reflection point is detected from one or more eye images among the eye images, the gaze calculator extracts the cornea central point using distance information between a pre-stored lighting reflection point and the cornea central point and the one lighting reflection point.

The gaze calculator may calculate distances from the cornea central point to the two or more lighting reflection points and accumulate and store calculated distance information.

The gaze calculator may convert 2D coordinates of the lighting reflection point and the pupil central point into 3D coordinates.

The gaze calculator may determine a lighting that forms the one lighting reflection point at a cornea among the two or more lightings using a face direction vector.

The gaze calculator may calculate similarity between lighting reflection points in an eye image from which two or more lighting reflection points are detected and an eye image from which one lighting reflection point is detected among the eye images, and determine a lighting that forms the one lighting reflection point at a cornea.

The gaze calculator may calculate a vector for connection between the one lighting reflection point and the determined lighting and extract the cornea central point using the calculated vector and the distance information.

The distance information may be obtained by calculating an average distance of distance information for a predetermined recent period among distance information items from a pre-stored cornea central point to a lighting reflection point.

A method for tracking gaze of a gaze tracker including two or more cameras and two or more lightings includes acquiring eye images of a user using the two or more cameras, detecting a lighting reflection point from each of the eye images, upon detecting two or more lighting reflection points from each of the eye images, calculating vectors for connection between each lighting and a lighting reflection point corresponding thereto and detecting an intersection point between the calculated vectors as a cornea central point, upon only one lighting reflection point from one or more eye images among the eye images, detecting the cornea central point using distance information between a pre-stored lighting reflection point and the cornea central point and the one lighting reflection point, upon detecting the cornea central point, extracting a pupil central point from the eye image, and calculating a gaze vector using the cornea central point and the pupil central point.

The detecting of the lighting reflection point may include converting 2D coordinates of the lighting reflection point into 3D coordinates.

The detecting of the intersection point of the vectors as the cornea central point may include calculating distances from the cornea central point to the two or more lighting reflection points and accumulating and storing calculated distance information.

The detecting of the cornea central point using the one lighting reflection point may include determining a lighting corresponding to the one lighting reflection point, calculating a first vector for connection between the one lighting reflection point and the determined lighting, and extracting the cornea central point using the first vector and the distance information.

The determining of the lighting corresponding to the one lighting reflection point may include determining a lighting that forms the one lighting reflection point at a cornea among the two or more lightings using a face direction vector.

The determining of the lighting corresponding to the one lighting reflection point may include calculating similarity between lighting reflection points in an eye image from which two or more lighting reflection points are detected and an eye image from which one lighting reflection point is detected and determining a lighting that forms the one lighting reflection point at a cornea.

The distance information may be obtained by calculating an average distance of distance information for a predetermined recent period among distance information items from a pre-stored cornea central point to a lighting reflection point.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
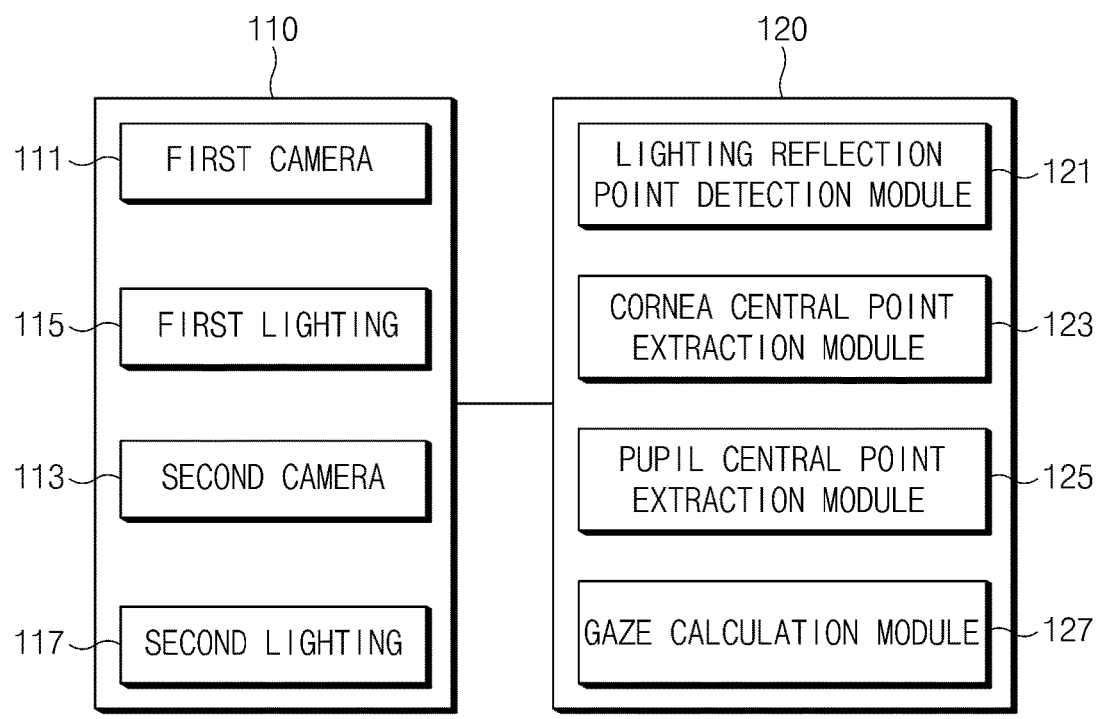
FIG. 1 is a block diagram of a gaze tracker.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

It will be further understood that the terms "comprises" and/or "comprising" when used in this specification, specify the presence of stated components, but do not preclude the presence or addition of other components.

Also, the terms, such as 'unit' or 'module', etc., should be understood as a unit that processes at least one function or operation and that may be embodied in a hardware manner, a software manner, or a combination of the hardware manner and the software manner. As used herein, the singular forms "a", "an" and "the" are intended to include the plural forms as well, unless the context clearly indicates otherwise.

A gaze tracker according to the present disclosure includes two or more cameras and two or more lightings but an example in which the gaze tracker includes two cameras and two lightings will be described for understanding the present disclosure.

FIG. 1 is a block diagram of a gaze tracker.

As illustrated in FIG. 1, the gaze tracker may include an image acquirer 110 and a gaze calculator 120.

The image acquirer 110 may be a stereo camera and may acquire user left and right eye images. The image acquirer 110 may include a first camera 111, a second camera 113, a first lighting 115, and a second lighting 117.

The first camera 111 and the second camera 113 may simultaneously photograph the same subject (a user eye) at different positions. In other words, the image acquirer 110 may acquire two eye images with respect to left and right eyes of a user, respectively. When the images are captured through the first camera 111 and the second camera 113, the first lighting 115 and the second lighting 117 may emit infrared rays to user eyes.

The first camera 111 and the second camera 113 may be embodied as an infrared camera including an infrared filter. In addition, the first lighting 115 and the second lighting 117 may be embodied as a light emitting diode (LED), a lamp, or the like for emitting infrared rays, or the like.

Although the image acquirer 110 photographs a user eye, the present disclosure is not limited thereto, and the image acquirer 110 may be configured to photograph a user face and to extract an eye region from the face image captured by an image processor.

The gaze calculator 120 may calculate user gaze from eye images acquired through the image acquirer 110. The gaze calculator 120 may include a lighting reflection point detection module 121, a cornea central point extraction module 123, a pupil central point extraction module 125, and a gaze calculation module 127.

The lighting reflection point detection module 121 may detect a lighting reflection point generated by the first lighting 115 and/or the second lighting 117 from each eye image captured by the first camera 111 and the second camera 113. In other words, the lighting reflection point detection module 121 may detect the lighting reflection point generated by the first lighting 115 and/or the second lighting 117 from the eye image captured by the first camera 111. In addition, the lighting reflection point detection module 121 may detect the lighting reflection point generated by the first lighting 115 and/or the second lighting 117 from the eye image captured by the second camera 113.

The lighting reflection point detection module 121 may convert 2D coordinates of the detected lighting reflection points into 3D coordinates using 3D restoration technologies such as triangulation. For example, coordinates of a first lighting reflection point generated by the first lighting 115 may be extracted from a first eye image and a second eye image which are captured by the first camera 111 and the second camera 113, and 3D coordinates of the first lighting reflection point may be calculated using the coordinates of the first lighting reflection point extracted from the first eye image and the coordinates of the first lighting reflection point extracted from the second eye image.

In addition, the lighting reflection point detection module 121 may detect a lighting reflection point using a high pass filter.

Figure 2:
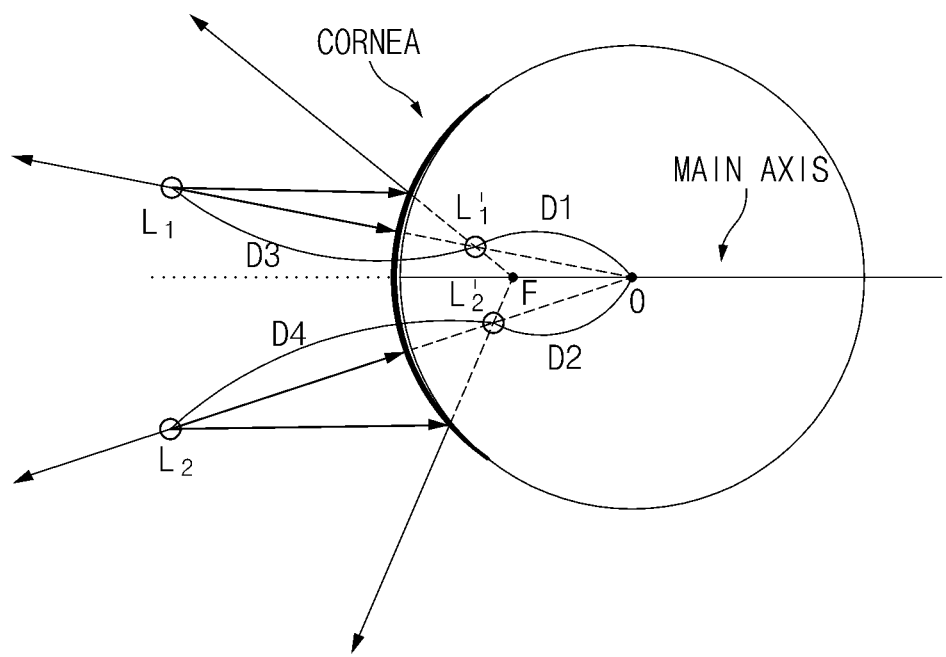
FIG. 2 is a diagram for explanation of extraction of a cornea central point.

Referring to FIG. 2, when actual position coordinates of the first lighting 115 and the second lighting 117 are L1 and L2, respectively, the lighting reflection point detection module 121 may calculate 3D coordinates L1' and L2' of the first lighting reflection point and the second lighting reflection point that are formed at the cornea by the first lighting 115 and the second lighting 117.

The cornea central point extraction module 123 may calculate a cornea central point using the detected lighting reflection point (the first lighting reflection point and/or the second lighting reflection point) and position coordinates of lightings 115 and/or 117 corresponding to the detected lighting reflection point. In other words, the cornea central point extraction module 123 may calculate a first vector (straight line D3) for connection between a 3D coordinate L1' of the first lighting reflection point and an actual position coordinate L1 of the first lighting 115. In addition, the cornea central point extraction module 123 may calculate a second vector (straight line D4) for connection between a 3D coordinate L2' of the second lighting reflection point and an actual position coordinate L2 of the second lighting 117. The cornea central point extraction module 123 may extract an intersection point between the first vector and the second vector as a cornea central point O.

The cornea central point extraction module 123 may extract the cornea central point O and then calculate distances D1 and D2 to the first lighting reflection point L1' and the second lighting reflection point L2' from the cornea central point O. In addition, the cornea central point extraction module 123 may accumulate and store the calculated distance information in a storage (not shown). Here, the distance information may be stored in the form of Table 1 below.

TABLE 1

| Frame # | Right eye image | | Left eye image | |
|---------|-----|-----|-----|-----|
|         | D1  | D2  | D1  | D2  |
| Frame 1 | 22 mm | 21 mm | 20 mm | 17 mm |
| Frame 2 | 25 mm | 25 mm | 22 mm | 24 mm |
| . | . | . | . | . |
| . | . | . | . | . |
| . | . | . | . | . |

Upon detecting one lighting reflection point, the cornea central point extraction module 123 may calculate an average distance of distance information for a predetermined recent period of distance information between the cornea central point and the first lighting reflection point detected from previous eye images pre-stored in a storage (not shown). For example, the cornea central point extraction module 123 may calculate an average of distances between the cornea central point and the first lighting reflection points detected from five recent frames.

In addition, the cornea central point extraction module 123 may calculate an average distance of distance information for a predetermined recent period of distance information between the cornea central point and the second lighting reflection point detected from previous eye images pre-stored in a storage (not shown).

Although an average distance of distance information for a predetermined recent period of pre-stored distance information is calculated and used has been described, the present disclosure is not limited thereto, and most recent distance information of pre-stored distance information may be used.

When only one lighting reflection point is detected by the lighting reflection point detection module 121, the cornea central point extraction module 123 may check a lighting that forms the detected lighting reflection point at the cornea among the first lighting 115 and the second lighting 117.

In this case, the cornea central point extraction module 123 may determine whether the detected lighting reflection point is the first lighting reflection point formed at the cornea by the first lighting 115 or the second lighting reflection point formed at the cornea by the second lighting 117 using a face direction vector. The face direction vector may be calculated from a user face image acquired through the image acquirer 110.

The cornea central point extraction module 123 may calculate similarity between lighting reflection points in an eye image from which two or more lighting reflection points are detected and an eye image from which one lighting reflection point is detected and determine a lighting that forms the detected one lighting reflection point at the cornea among the first lighting 115 and the second lighting 117.

For example, when the first lighting reflection point is positioned away from a pupil central point to the left by three pixels and the second lighting reflection point is positioned away from the pupil central point to the right by three pixels in an eye image from which the two lighting reflection points are detected, a distance between the one detected lighting reflection point and the pupil central point may be calculated, and whether the one detected lighting reflection point is positioned away from the pupil central point to the left or the right may be determined based on the calculated distance.

The cornea central point extraction module 123 may calculate a third vector for connection between the first lighting reflection point and the first lighting 115 when the detected lighting reflection point is the first lighting reflection point. In addition, the cornea central point extraction module 123 may calculate a cornea central point using the third vector and an average distance between the first lighting reflection point and the cornea central point.

When the detected lighting reflection point is the second lighting reflection point, the cornea central point extraction module 123 may calculate the third vector for connection between the second lighting reflection point and the second lighting 117. In addition, the cornea central point extraction module 123 may calculate the cornea central point using the third vector and an average distance between the second lighting reflection point and the cornea central point.

The pupil central point extraction module 125 may image-process an eye image to detect the pupil central point. In this case, the pupil central point extraction module 125 may detect an eye region from the eye image acquired by the image acquirer 110 and detect the pupil central point from the detected eye region. The pupil central point extraction module 125 may restore the 2D pupil central point detected from the eye image to a 3D pupil central point.

The gaze calculation module 127 may calculate a gaze vector in which a user gazes using the pupil central point and the cornea central point. That is, the gaze calculation module 127 may calculate a straight line between the pupil central point and the cornea central point as the gaze vector.

Figure 3A:
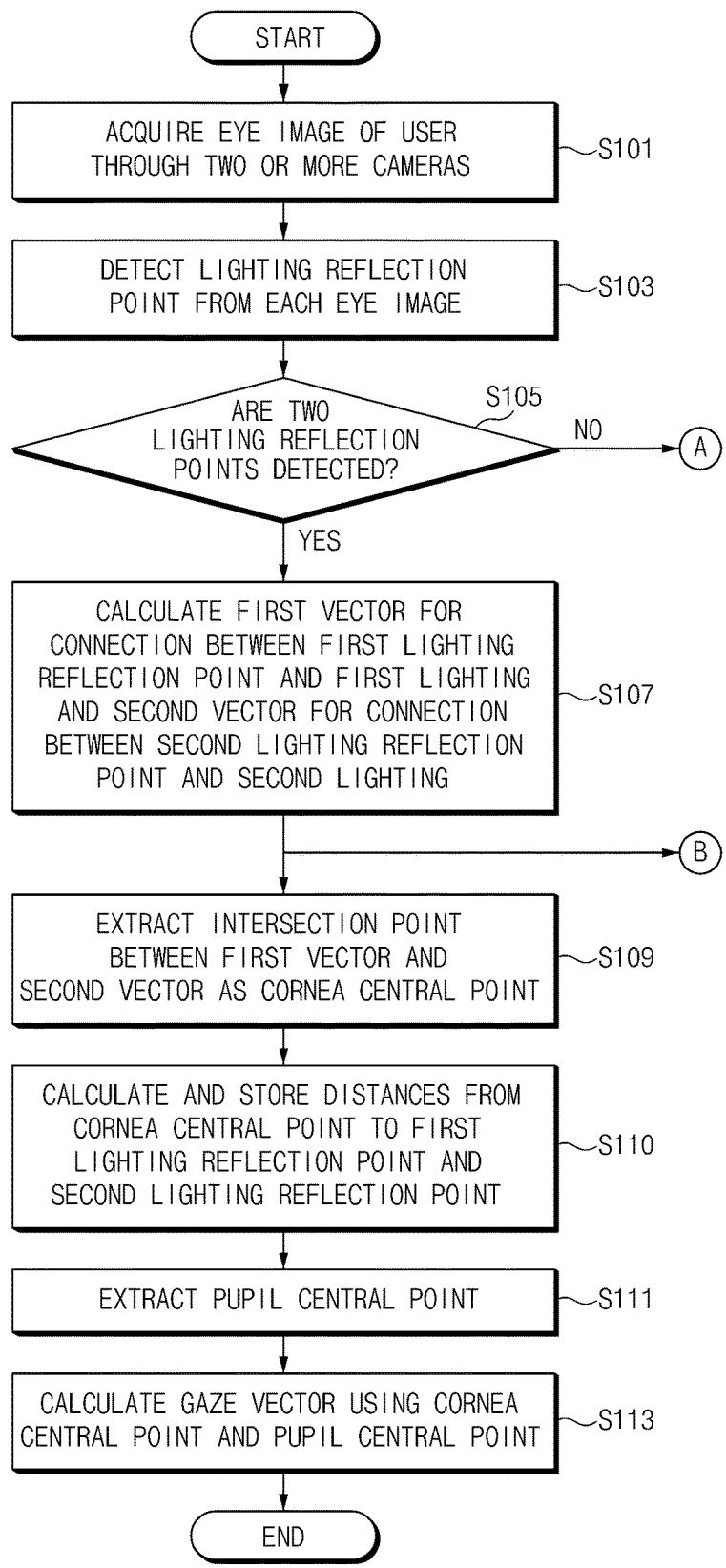
FIGS. 3A and 3B are flowcharts illustrating a gaze tracking method.
Figure 3B:
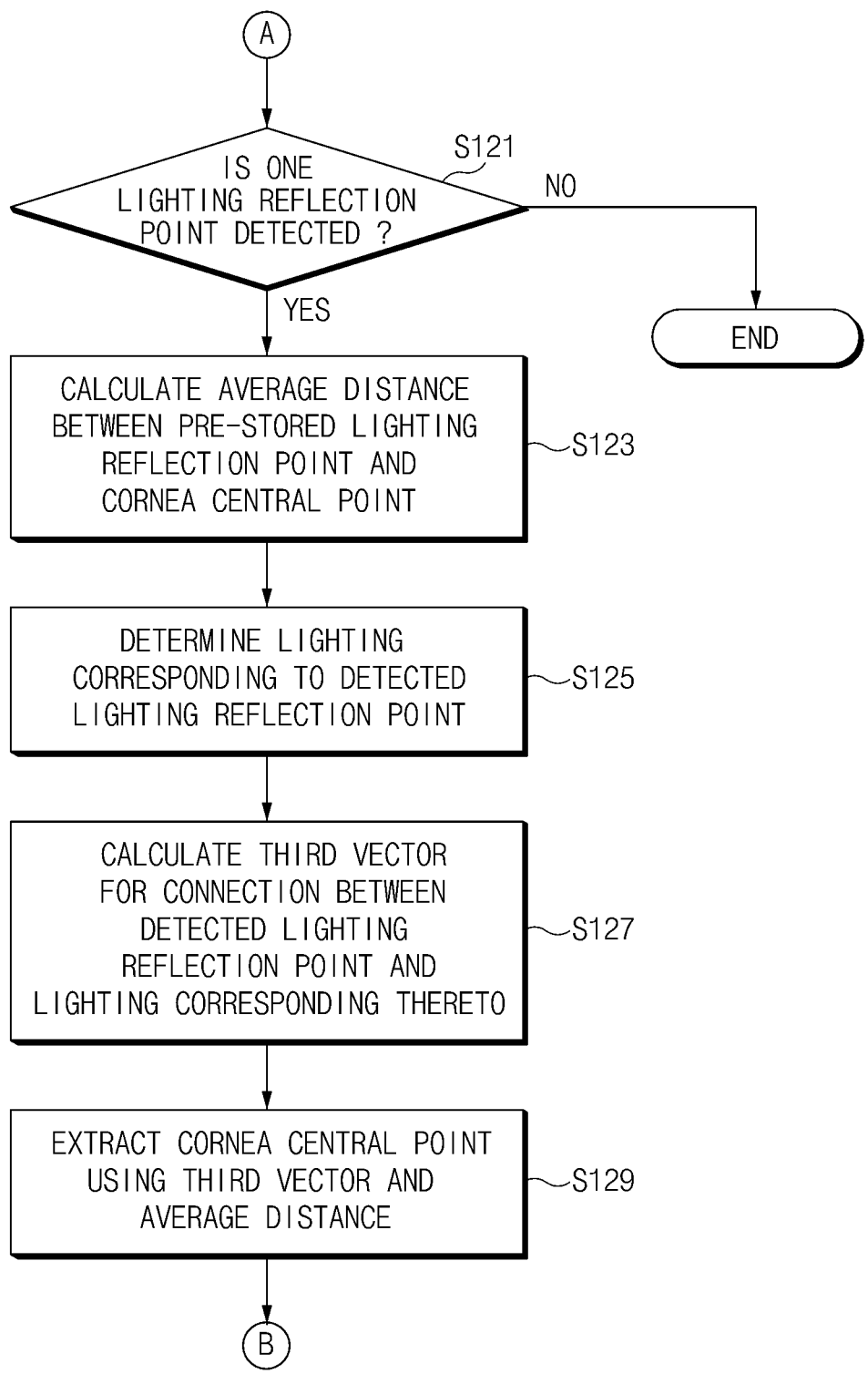

FIGS. 3A and 3B are flowcharts illustrating a gaze tracking method.

As illustrated in FIG. 3A, the gaze calculator 120 of the gaze tracker may acquire an eye image of the user through the image acquirer 110 (S101). In this case, the gaze calculator 120 may capture the eye image of the user through the first camera 111 and the second camera 113. In other words, the gaze tracker may acquire two images with respect to right and left eyes of the user, respectively.

The lighting reflection point detection module 121 of the gaze tracker may detect one or more lighting reflection points from the eye images output from the first camera 111 and the second camera 113 (S103). The lighting reflection point detection module 121 may covert 2D coordinates of the detected lighting reflection points into 3D coordinates using 3D restoration technologies such as triangulation.

The cornea central point extraction module 123 of the gaze tracker may check whether the two lighting reflection points are detected through the lighting reflection point detection module 121 (S105). In other words, the cornea central point extraction module 123 may check whether the first lighting reflection point and the second lighting reflection point that are formed on the cornea by the first lighting 115 and the second lighting 117 are detected.

When the two lighting reflection points are detected from the respective eye images, the cornea central point extraction module 123 may calculate vectors for connection between the respective detected lighting reflection points and the lightings 115 and 117 corresponding thereto (S107). In other words, the cornea central point extraction module 123 may calculate a first vector for connection between a 3D coordinate of the first lighting reflection point and an actual position coordinate of the first lighting 115 and a second vector for connection between a 3D coordinate of the second lighting reflection point and an actual position coordinate of the second lighting 117.

The cornea central point extraction module 123 may extract a point in which the calculated vectors intersect with each other as the cornea central point (S109). For example, the cornea central point extraction module 123 may extract the intersection point between the pre-calculated first vector and second vector as the cornea central point.

The cornea central point extraction module 123 may calculate and store distances from the cornea central point to the first lighting reflection point and the second lighting reflection point (S110).

When the cornea central point is extracted, the gaze tracker may extract the pupil central point from the eye image via image processing (S111). In this case, the pupil central point extraction module 125 may detect an eye region from the image acquired through the image acquirer 110 and detect the pupil central point from the eye region. In this case, the pupil central point extraction module 125 may restore a 2 D pupil central point into a 3D pupil central point. Although the pupil central point is extracted after the cornea central point is extracted, the present disclosure is not limited thereto, and the cornea central point and the pupil central point may be simultaneously detected.

The gaze calculation module 127 of the gaze tracker may calculate a straight line for connection between the cornea central point and the pupil central point as a gaze vector (S113).

When two lighting reflection points are not detected in operation S105, the gaze tracker may check whether the number of detected lighting reflection point is one (S121). The gaze tracker may check whether only one lighting reflection point is detected from one or more eye images among eye images acquired through the first camera 111 and the second camera 113.

When only one lighting reflection point is detected, the gaze tracker may calculate an average distance between a pre-stored lighting reflection point and the cornea central point (S123). The cornea central point extraction module 123 may calculate an average distance between the first lighting reflection point and the cornea central point and an average distance between the second lighting reflection point and the cornea central point for a predetermined recent period among distance information items to the first lighting reflection point and the second lighting reflection point from a pre-stored cornea central point.

The gaze tracker may determine a lighting corresponding to the detected lighting reflection point (S125). In this case, the gaze tracker may check a lighting that forms the detected lighting reflection point among the first lighting 115 and the second lighting 117 using a face direction vector.

The gaze tracker may calculate a third vector for connection between the detected lighting reflection point and a lighting corresponding thereto (S127). In other words, when the detected lighting reflection point is the first lighting reflection point, the cornea central point extraction module 123 may calculate a vector for connection between the first lighting reflection point and the first lighting 115. When the detected lighting reflection point is the second lighting reflection point, the cornea central point extraction module 123 may calculate a vector for connection between the second lighting 117 and the second lighting reflection point.

The gaze tracker may calculate the cornea central point using the third vector and the average distance (S129).

Then the gaze tracker may extract the pupil central point (S111) and calculate a gaze vector using the cornea central point and the pupil central point (S113).

Although the case in which S125 is performed after S123 is performed has been described thus far, S123 may be performed after S125 is performed.

For example, when the one detected lighting reflection point is the first lighting reflection point, the cornea central point extraction module 123 may calculate an average distance of distance information for a predetermined recent period among distance information items between the cornea central point and the first lighting reflection point detected from previous eye images pre-stored in a storage (not shown).

When the one detected lighting reflection point is the second lighting reflection point, the cornea central point extraction module 123 may calculate an average distance of distance information for a predetermined recent period among distance information items between the cornea central point and the second lighting reflection point detected from previous eye images pre-stored in a storage (not shown).

When only one lighting reflection point is detected from an eye image, a lighting that generates the detected lighting reflection point may be determined using a face direction vector, but the present disclosure is not limited thereto.

For example, when one lighting reflection point is detected from one eye image and two lighting reflection points are detected from the other one eye image among two eye images acquired through two cameras, similarity between the lighting reflection points in the two eye images may be calculated and a lighting that generates the one detected lighting reflection point may be determined.

According to the present disclosure, when user gaze is tracked using a stereo camera including two cameras and two lightings, even if only one lighting reflection point is formed at the cornea, the user gaze may be tracked using only one lighting reflection point. Accordingly, a range for gaze tracking of the gaze tracker may be enlarged.

The present disclosure is not limited thereto, but may be variously modified and altered by those skilled in the art to which the present disclosure pertains without departing from the spirit and scope of the present disclosure claimed in the following claims.

What is claimed is:

1. A gaze tracker comprising:
   an image acquirer configured to acquire eye images of a user using at least two cameras and at least two lightings; and
   a processor configured to calculate a gaze to detect a lighting reflection point from each of the eye images and to extract a cornea central point, the processor configured to detect a pupil central point from each of the eye images and calculate a gaze vector using the cornea central point and the pupil central point,
   wherein, when at least two lighting reflection points are detected from each of the eye images, the processor is configured to calculate vectors for connection between each lighting and the lighting reflection point corresponding thereto and to detect an intersection point between the calculated vectors as the cornea central point, and when only one lighting reflection point is detected from one or more eye images among the eye images, the processor is configured to extract the cornea central point using distance information between a pre-stored lighting reflection point and the cornea central point and the one lighting reflection point.

2. The gaze tracker according to claim 1, wherein the processor is configured to calculate distances from the cornea central point to the at least two lighting reflection points and to accumulate and store calculated distance information.

3. The gaze tracker according to claim 1, wherein the processor is configured to convert 2D coordinates of the lighting reflection point and the pupil central point into 3D coordinates.

4. The gaze tracker according to claim 1, wherein the processor is configured to determine a lighting that forms the one lighting reflection point at a cornea among the at least two lightings using a face direction vector.

5. The gaze tracker according to claim 4, wherein the processor is configured to calculate a vector for connection between the one lighting reflection point and the determined lighting and extract the cornea central point using the calculated vector and the distance information.

6. The gaze tracker according to claim 1, wherein the processor is configured to calculate similarity between lighting reflection points in an eye image from which the at least two lighting reflection points are detected and an eye image from which one lighting reflection point is detected among the eye images, and to determine a lighting that forms the one lighting reflection point at a cornea.

7. The gaze tracker according to claim 1, wherein the processor is configured to obtain the distance information by calculating an average distance of distance information for a predetermined recent period among distance information items from a pre-stored cornea central point to a lighting reflection point.

8. A method for tracking gaze of a gaze tracker comprising at least two cameras and at least two lightings, the method comprising:
   acquiring eye images of a user using the at least two cameras;
   detecting a lighting reflection point from each of the eye of the images;
   upon detecting at least two lighting reflection points from each of the eye images, calculating vectors for connection between each lighting and a lighting reflection point corresponding thereto and detecting an intersection point between the calculated vectors as a cornea central point;
   upon only one lighting reflection point from one or more eye images among the eye images, detecting the cornea central point using distance information between a pre-stored lighting reflection point and the cornea central point and the one lighting reflection point;
   upon detecting the cornea central point, extracting a pupil central point from the eye image; and
   calculating a gaze vector using the cornea central point and the pupil central point.

9. The method according to claim 8, wherein the detecting of the lighting reflection point includes converting 2D coordinates of the lighting reflection point into 3D coordinates.

10. The method according to claim 8, wherein the detecting of the intersection point of the vectors as the cornea central point includes calculating distances from the cornea central point to the at least two lighting reflection points and accumulating and storing calculated distance information.

11. The method according to claim 8, wherein the detecting of the cornea central point using the one lighting reflection point comprises:
   determining a lighting corresponding to the one lighting reflection point;
   calculating a first vector for connection between the one lighting reflection point and the determined lighting; and
   extracting the cornea central point using the first vector and the distance information.

12. The method according to claim 11, wherein the determining of the lighting corresponding to the one lighting reflection point comprises determining a lighting that forms the one lighting reflection point at a cornea among the at least two lightings using a face direction vector.

13. The method according to claim 11, wherein the determining of the lighting corresponding to the one lighting reflection point comprises calculating similarity between lighting reflection points in an eye image from which two or more lighting reflection points are detected and an eye image from which one lighting reflection point is detected and determining a lighting that forms the one lighting reflection point at a cornea.

14. The method according to claim 8, wherein the distance information is obtained by calculating an average distance of distance information for a predetermined recent period among distance information items from a pre-stored cornea central point to a lighting reflection point.

* * * * *